(12) United States Patent
Chen (10) Patent No.: US 7,511,031 B2
(45) Date of Patent: Mar. 31, 2009

(54) NONINVASIVE VASCULAR THERAPY

(75) Inventor: James Chen, Bellevue, WA (US)

(73) Assignee: Lights Sciences Oncology, Inc., Snoqualmie, WA (US)

( * ) Notice: Subject to any disclaimer, the term of this patent is extended or adjusted under 35 U.S.C. 154(b) by 520 days.

(21) Appl. No.: 10/899,834

(22) Filed: Jul. 26, 2004

(65) Prior Publication Data

US 2005/0004510 A1 Jan. 6, 2005

Related U.S. Application Data (62) Division of application No. 09/905,777, filed on Jul. 13, 2001.

(60) Provisional application No. 60/116,235, filed on Jan. 15, 1999.

(51) Int. Cl.
- A61K 9/127 (2006.01)
- A61N 1/30 (2006.01)
- A61N 5/06 (2006.01)
- A61N 5/067 (2006.01)
- A61M 35/00 (2006.01)
- A61F 13/00 (2006.01)
- A61K 39/395 (2006.01)

(52) U.S. Cl. .................... 514/185; 424/9.362; 424/411; 424/450; 604/19; 604/20; 604/290; 604/304; 607/88; 607/89; 607/90; 607/91; 607/108

(58) Field of Classification Search ........................ None
See application file for complete search history.

(56) References Cited

U.S. PATENT DOCUMENTS

| | | | |
|---|---|---|---|
| 4,337,759 A | 7/1982 | Popovich et al. | 126/438 |
| 4,577,636 A | 3/1986 | Spears | 128/654 |
| 4,675,338 A | 6/1987 | Bommer et al. | 514/410 |
| 4,690,492 A | 9/1987 | Beard | 350/96.2 |
| 4,693,556 A | 9/1987 | McCaughan, Jr. | 350/320 |
| 4,693,885 A | 9/1987 | Bommer et al. | 424/2 |
| 4,753,958 A | 6/1988 | Weinstein et al. | 514/410 |
| 4,823,244 A | 4/1989 | Alaybayoglu et al. | 362/194 |
| 4,849,207 A | 7/1989 | Sakata et al. | 424/1.1 |
| 4,852,567 A | 8/1989 | Sinofsky | 128/303.1 |
| 4,861,876 A | 8/1989 | Kessel | 540/145 |
| 4,866,168 A | 9/1989 | Dougherty et al. | 540/145 |
| 4,878,891 A | 11/1989 | Judy et al. | 604/5 |
| 4,907,132 A * | 3/1990 | Parker | 362/556 |
| 4,925,736 A | 5/1990 | Shikowitz | 424/449 |
| 4,932,934 A | 6/1990 | Dougherty et al. | 604/21 |
| 4,935,498 A | 6/1990 | Sessler et al. | 534/15 |
| 4,957,481 A | 9/1990 | Gatenby | 604/20 |
| 4,973,848 A | 11/1990 | Kolobanov et al. | 250/458.1 |
| 4,986,628 A | 1/1991 | Lozhenko et al. | 350/96.29 |
| 4,997,639 A | 3/1991 | Aizawa et al. | 424/9 |
| 4,998,930 A | 3/1991 | Lundahl | 606/15 |
| 5,002,962 A | 3/1991 | Pandey et al. | 514/410 |
| 5,026,367 A | 6/1991 | Leckrone et al. | 606/7 |
| 5,028,594 A | 7/1991 | Carson | 514/23 |
| 5,041,078 A | 8/1991 | Matthes et al. | 604/4 |
| 5,048,524 A | 9/1991 | Bailey et al. | 128/634 |
| 5,053,006 A | 10/1991 | Watson | 604/52 |
| 5,095,030 A | 3/1992 | Levy et al. | 514/410 |
| 5,171,749 A | 12/1992 | Levy et al. | 514/410 |
| 5,190,536 A | 3/1993 | Wood et al. | 606/16 |
| 5,259,380 A | 11/1993 | Mendes et al. | 607/115 |
| 5,263,925 A | 11/1993 | Gilmore et al. | 604/4 |
| 5,283,255 A | 2/1994 | Levy et al. | 514/410 |
| 5,298,018 A | 3/1994 | Narciso, Jr. | 604/21 |
| 5,308,861 A | 5/1994 | Aizawa et al. | 514/410 |
| 5,314,905 A | 5/1994 | Pandey et al. | 514/410 |
| 5,330,741 A | 7/1994 | Smith et al. | 424/9 |
| 5,344,434 A | 9/1994 | Talmore | 607/88 |
| 5,368,841 A | 11/1994 | Trauner et al. | 424/9 |
| 5,399,583 A | 3/1995 | Levy et al. | 514/410 |
| 5,430,051 A | 7/1995 | Aizawa et al. | 514/410 |
| 5,441,531 A | 8/1995 | Zarate et al. | 607/90 |

(Continued)

FOREIGN PATENT DOCUMENTS

AU 0 674 251 12/1996

(Continued)

OTHER PUBLICATIONS

Adili et al., "Local delivery of photosensitizing drugs in arteries: a novel approach to photodynamic therapy for the prevention of intimal hyperplasia", *Proc. SPIE-INT, Soc. Opt. Eng.*, 2395:402-408 (1995) (Ger. Symp. Laser Angioplasty, 2nd, 1980).

(Continued)

*Primary Examiner*—Karen A Canella
(74) *Attorney, Agent, or Firm*—Seed Intellectual Property Law Group PLLC (57) ABSTRACT

The present invention is drawn to apparatus for transcutaneous photodynamic therapy ("PDT") of a target tissue or compositions in a mammalian subject, which includes a light source that is external to the subject and is selected from among one or a plurality of laser diodes; light emitting diodes; electroluminescent light source; incandescent light sources; cold cathode fluorescent light sources; organic polymer light sources; or inorganic light sources, where the light source is adapted to direct the light in a direction lengthwise and parallel to a vessel wall comprising the lesion.

25 Claims, 2 Drawing Sheets

U.S. PATENT DOCUMENTS

| | | | |
|---|---|---|---|
| 5,445,608 A | 8/1995 | Chen et al. | 604/20 |
| 5,454,794 A | 10/1995 | Narciso et al. | 604/280 |
| 5,456,661 A | 10/1995 | Narciso, Jr. | 604/20 |
| 5,474,528 A | 12/1995 | Meserol | 604/20 |
| 5,474,765 A | 12/1995 | Thorpe | 424/178.17 |
| 5,482,698 A | 1/1996 | Griffiths | 424/1.41 |
| 5,484,778 A | 1/1996 | Kenney et al. | 514/63 |
| 5,484,803 A | 1/1996 | Richter | 514/410 |
| 5,494,793 A | 2/1996 | Schindele et al. | 435/6 |
| 5,498,710 A | 3/1996 | Pandey et al. | 540/145 |
| 5,500,009 A | 3/1996 | Mendes et al. | 607/88 |
| 5,514,669 A | 5/1996 | Selman | 514/63 |
| 5,519,534 A | 5/1996 | Smith et al. | 359/599 |
| 5,534,506 A | 7/1996 | Morgan et al. | 514/185 |
| 5,543,514 A | 8/1996 | Sessler et al. | 540/472 |
| 5,549,660 A | 8/1996 | Mendes et al. | 607/88 |
| 5,556,612 A | 9/1996 | Anderson et al. | 424/59 |
| 5,565,552 A | 10/1996 | Magda et al. | 534/11 |
| 5,567,409 A | 10/1996 | Aizawa et al. | 424/9.363 |
| 5,571,152 A | 11/1996 | Chen et al. | 607/92 |
| 5,576,013 A * | 11/1996 | Williams et al. | 424/423 |
| 5,591,847 A | 1/1997 | Pandey et al. | 540/472 |
| 5,591,855 A | 1/1997 | Hudkins et al. | 546/256 |
| 5,594,136 A | 1/1997 | Sessler et al. | 540/472 |
| 5,616,140 A | 4/1997 | Prescott | 606/10 |
| 5,620,439 A | 4/1997 | Abela et al. | 606/11 |
| 5,630,996 A | 5/1997 | Reno et al. | 424/1.49 |
| 5,634,711 A | 6/1997 | Kennedy et al. | 362/119 |
| 5,643,334 A | 7/1997 | Eckhouse et al. | 607/88 |
| 5,645,562 A | 7/1997 | Hann et al. | 606/194 |
| 5,655,832 A | 8/1997 | Pelka et al. | 362/296 |
| 5,686,113 A | 11/1997 | Speaker et al. | 424/490 |
| 5,698,866 A | 12/1997 | Doiron et al. | 257/99 |
| 5,700,243 A | 12/1997 | Nariso, Jr. | 604/20 |
| 5,702,432 A | 12/1997 | Chen et al. | 607/88 |
| 5,705,518 A | 1/1998 | Richter et al. | 514/410 |
| 5,707,401 A | 1/1998 | Talmore | 607/88 |
| 5,709,653 A | 1/1998 | Leone | 604/20 |
| 5,715,837 A | 2/1998 | Chen | 128/899 |
| 5,736,563 A | 4/1998 | Richter | 514/410 |
| 5,741,316 A | 4/1998 | Chen et al. | 607/61 |
| 5,746,494 A | 5/1998 | Koeda et al. | 362/32 |
| 5,766,222 A | 6/1998 | Petit | 606/234 |
| 5,766,234 A | 6/1998 | Chen et al. | 607/92 |
| 5,769,844 A | 6/1998 | Ghaffari | 606/16 |
| 5,770,619 A | 6/1998 | Richter et al. | 514/410 |
| 5,770,730 A | 6/1998 | Pandey et al. | 540/472 |
| 5,775,339 A | 7/1998 | Woodburn et al. | 128/898 |
| 5,776,175 A | 7/1998 | Eckhouse et al. | 607/100 |
| 5,776,427 A | 7/1998 | Thorpe et al. | 424/1.49 |
| 5,782,896 A | 7/1998 | Chen et al. | 607/88 |
| 5,797,868 A | 8/1998 | Leone | 604/21 |
| 5,798,349 A | 8/1998 | Levy et al. | 514/185 |
| 5,800,432 A | 9/1998 | Swanson | 606/49 |
| 5,800,478 A | 9/1998 | Chen et al. | 607/88 |
| 5,807,881 A | 9/1998 | Leong et al. | 514/410 |
| 5,811,248 A | 9/1998 | Ditlow et al. | 435/7.9 |
| 5,814,008 A | 9/1998 | Chen et al. | 604/21 |
| 5,817,048 A | 10/1998 | Lawandy | 604/20 |
| 5,824,080 A | 10/1998 | Lamuraglia | 623/11 |
| 5,827,186 A | 10/1998 | Chen et al. | 600/407 |
| 5,829,448 A | 11/1998 | Fisher et al. | 128/898 |
| 5,832,931 A | 11/1998 | Wachter et al. | 128/898 |
| 5,835,648 A | 11/1998 | Narciso, Jr. et al. | 385/31 |
| 5,843,143 A | 12/1998 | Whitehurst | 607/88 |
| 5,849,027 A | 12/1998 | Gart et al. | 607/93 |
| 5,851,225 A | 12/1998 | Lawandy | 607/88 |
| 5,855,866 A | 1/1999 | Thorpe et al. | 424/1.49 |
| 5,863,538 A | 1/1999 | Thorpe et al. | 424/136.1 |
| 5,864,035 A | 1/1999 | Pandey et al. | 540/472 |
| 5,865,840 A | 2/1999 | Chen | 607/92 |
| 5,876,427 A | 3/1999 | Chen et al. | 607/88 |
| 5,882,328 A | 3/1999 | Levy et al. | 604/20 |
| 5,906,579 A | 5/1999 | Vander Salm et al. | 600/424 |
| 5,912,257 A | 6/1999 | Prasad et al. | 514/356 |
| 5,913,834 A | 6/1999 | Francais | 600/591 |
| 5,913,884 A | 6/1999 | Trauner et al. | 607/88 |
| 5,921,244 A | 7/1999 | Chen et al. | 128/897 |
| 5,929,105 A | 7/1999 | Sternberg et al. | 514/410 |
| 5,942,534 A | 8/1999 | Trauner et al. | 514/410 |
| 5,944,748 A | 8/1999 | Mager et al. | 607/88 |
| 5,945,762 A | 8/1999 | Chen et al. | 310/171 |
| 5,952,329 A | 9/1999 | Cincotta et al. | 514/224.5 |
| 5,957,960 A | 9/1999 | Chen et al. | 607/92 |
| 5,976,175 A | 11/1999 | Hirano et al. | 607/89 |
| 5,976,535 A | 11/1999 | Fritzberg et al. | 424/182.1 |
| 5,989,245 A | 11/1999 | Prescott | 606/14 |
| 5,997,569 A | 12/1999 | Chen et al. | 607/88 |
| 5,997,842 A | 12/1999 | Chen | 424/1.29 |
| 5,998,597 A | 12/1999 | Fisher et al. | 536/23.1 |
| 6,013,053 A | 1/2000 | Bower et al. | 604/96 |
| 6,015,897 A | 1/2000 | Theodore et al. | 540/474 |
| 6,021,347 A | 2/2000 | Herbst et al. | 607/2 |
| 6,036,941 A | 3/2000 | Bottiroli et al. | 424/9.6 |
| 6,042,603 A | 3/2000 | Fisher et al. | 607/89 |
| 6,048,359 A | 4/2000 | Biel | 607/92 |
| 6,051,230 A | 4/2000 | Thorpe et al. | 424/178.1 |
| 6,058,937 A | 5/2000 | Doiron et al. | 128/898 |
| 6,063,108 A | 5/2000 | Salansky et al. | 607/89 |
| 6,071,944 A | 6/2000 | Rodgers et al. | 514/408 |
| 6,080,160 A | 6/2000 | Chen et al. | 606/72 |
| 6,083,485 A | 7/2000 | Licha et al. | 424/9.6 |
| 6,090,788 A | 7/2000 | Lurie | 514/23 |
| 6,092,531 A | 7/2000 | Chen et al. | 128/899 |
| 6,095,147 A * | 8/2000 | Hill et al. | 128/898 |
| 6,096,066 A | 8/2000 | Chen et al. | 607/88 |
| 6,100,290 A | 8/2000 | Levy et al. | 514/410 |
| 6,100,893 A | 8/2000 | Ensz et al. | 345/420 |
| 6,107,325 A | 8/2000 | Chan et al. | 514/410 |
| 6,107,466 A | 8/2000 | Hasan et al. | 530/351 |
| 6,117,862 A | 9/2000 | Margaron et al. | 514/185 |
| 6,123,923 A | 9/2000 | Unger et al. | 424/9.52 |
| 6,138,681 A | 10/2000 | Chen et al. | 128/899 |
| 6,152,951 A | 11/2000 | Hashimoto et al. | 607/92 |
| 6,162,242 A | 12/2000 | Peyman | 607/88 |
| 6,165,440 A | 12/2000 | Esenaliev | 424/1.11 |
| 6,183,444 B1 | 2/2001 | Glines et al. | 604/187 |
| 6,187,030 B1 | 2/2001 | Gart et al. | 607/93 |
| 6,210,425 B1 | 4/2001 | Chen | 607/88 |
| 6,217,869 B1 | 4/2001 | Meyer et al. | 424/178.1 |
| 6,223,071 B1 | 4/2001 | Lundahl et al. | 600/476 |
| 6,238,426 B1 | 5/2001 | Chen | 607/88 |
| 6,273,904 B1 | 8/2001 | Chen et al. | 607/88 |
| 6,281,611 B1 | 8/2001 | Chen et al. | 310/171 |
| 6,297,228 B1 | 10/2001 | Clark et al. | 514/177 |
| 6,319,273 B1 | 11/2001 | Chen et al. | 607/88 |
| 6,331,744 B1 | 12/2001 | Chen et al. | 310/171 |
| 6,344,050 B1 | 2/2002 | Chen | 607/88 |
| 6,416,531 B2 | 7/2002 | Chen | 607/89 |
| 6,454,789 B1 | 9/2002 | Chen | 607/88 |
| 6,520,669 B1 | 2/2003 | Chen et al. | 362/545 |
| 6,534,040 B2 | 3/2003 | Pandey et al. | 424/9.362 |
| 6,554,853 B2 | 4/2003 | Chen | 607/88 |
| 6,580,228 B1 | 6/2003 | Chen et al. | 315/185 R |
| 6,602,274 B1 | 8/2003 | Chen | 607/88 |
| 6,624,187 B1 | 9/2003 | Pandey et al. | 514/410 |
| 6,657,351 B2 | 12/2003 | Chen et al. | 310/171 |
| 2001/0044623 A1 | 11/2001 | Chen | 606/2 |
| 2001/0046983 A1 | 11/2001 | Pandey et al. | 514/185 |
| 2001/0049502 A1 | 12/2001 | Chen | 604/167.06 |
| 2002/0010500 A1 | 1/2002 | Chen | 607/89 |
| 2002/0049247 A1 | 4/2002 | Chen | 514/410 |
| 2002/0087205 A1 | 7/2002 | Chen | 607/88 |
| 2002/0127224 A1 | 9/2002 | Chen | 424/130.1 |

| | | | |
|---|---|---|---|
| 2002/0127230 A1 | 9/2002 | Chen | 424/178.1 |
| 2002/0198576 A1 | 12/2002 | Chen | 607/88 |
| 2003/0018371 A1 | 1/2003 | Chen | 607/88 |
| 2003/0030342 A1 | 2/2003 | Chen et al. | 310/102 |
| 2003/0109813 A1 | 6/2003 | Chen | 60/2 |
| 2003/0114434 A1 | 6/2003 | Chen et al. | 514/185 |
| 2003/0167033 A1 | 9/2003 | Chen et al. | 604/20 |
| 2003/0208249 A1 | 11/2003 | Chen | 607/88 |
| 2004/0044197 A1 | 3/2004 | Pandey et al. | 540/140 |
| 2004/0044198 A1 | 3/2004 | Pandey et al. | 540/145 |

FOREIGN PATENT DOCUMENTS

| | | |
|---|---|---|
| AU | 0 694 868 | 7/1998 |
| AU | 0 708 410 | 8/1999 |
| AU | 0 713 227 | 11/1999 |
| AU | 0 720 815 | 6/2000 |
| AU | 0 721 857 | 7/2000 |
| EP | 0 407 122 | 1/1991 |
| EP | 0 407 155 | 1/1991 |
| EP | 0 175 617 | 10/1991 |
| EP | 1 334 748 A1 | 8/2003 |
| GB | 2 323 284 | 9/1998 |
| JP | 53-084998 | 7/1978 |
| JP | 57-185220 | 11/1982 |
| WO | 92/00106 | 1/1992 |
| WO | 93/00005 | 1/1993 |
| WO | 93/11657 | 6/1993 |
| WO | 93/13769 | 7/1993 |
| WO | 93/24127 | 12/1993 |
| WO | 95/32001 | 11/1995 |
| WO | 96/06641 | 3/1996 |
| WO | 97/31582 | 9/1997 |
| WO | 97/32520 | 9/1997 |
| WO | 97/32885 | 9/1997 |
| WO | 97/40679 | 11/1997 |
| WO | 97/46262 | 12/1997 |
| WO | 98/06456 | 2/1998 |
| WO | 98/08565 | 3/1998 |
| WO | 98/14243 | 4/1998 |
| WO | 98/20936 | 5/1998 |
| WO | 98/24371 | 6/1998 |
| WO | 98/24510 | 6/1998 |
| WO | 98/32491 | 7/1998 |
| WO | 98/32492 | 7/1998 |
| WO | 98/32493 | 7/1998 |
| WO | 98/33251 | 7/1998 |
| WO | 98/46130 | 10/1998 |
| WO | 98/47541 | 10/1998 |
| WO | 98/50034 | 11/1998 |
| WO | 98/50387 | 11/1998 |
| WO | 98/52610 | 11/1998 |
| WO | 98/56302 | 12/1998 |
| WO | 99/03503 | 1/1999 |
| WO | 94/06424 | 3/1999 |
| WO | 99/18879 | 4/1999 |
| WO | 99/20346 | 4/1999 |
| WO | 99/39769 | 8/1999 |
| WO | 99/52565 | 10/1999 |
| WO | 99/58149 | 11/1999 |
| WO | 99/66988 | 12/1999 |
| WO | 99/67248 | 12/1999 |
| WO | 99/67249 | 12/1999 |
| WO | 00/15296 | 3/2000 |
| WO | 00/36983 | 6/2000 |
| WO | 00/41725 | 7/2000 |
| WO | 00/41726 | 7/2000 |
| WO | 00/41727 | 7/2000 |
| WO | 00/41768 | 7/2000 |
| WO | 00/52793 | 9/2000 |
| WO | 00/15694 | 10/2000 |
| WO | 01/03770 | 1/2001 |
| WO | 01/05316 | 1/2001 |
| WO | 01/15694 | 3/2001 |
| WO | 01/015694 | 3/2001 |
| WO | 01/43825 | 6/2001 |
| WO | 01/51087 | 7/2001 |
| WO | 01/78216 | 10/2001 |
| WO | 01/78458 | 10/2001 |
| WO | 01/98708 | 12/2001 |
| WO | 02/17690 | 2/2002 |
| WO | 03/052793 | 6/2003 |
| WO | 03/061696 | 7/2003 |
| WO | 2004/002476 | 1/2004 |
| WO | 2004/005289 | 1/2004 |

OTHER PUBLICATIONS

Anonymous (1997) http://www.lumacare.com/. 2 pages.
Barr et al., "Normal Tissue Damage Following Photodynamic Therapy: Are There Biological Advantages?",Photodynamic Therapy, Basic Principles and Clinical Applications, Henderson, Barbara W. Dougherty, Thomas J., (Eds.); Marcel Dekker, Inc., New York; pp. 201-216.
Bayer et al., "Raw eggs and cancer therapy", *Science Spectra*, 12:34-41 (1998).
Beems et al., Photosensitizing properties of bacteriochlorophyllin a and bacteriochlorin a, two derivatives of bacteriochlorophyll α, *Photochem. Photobiol.* 46(5): 639-643 (1987).
Bellnier et al., Murine pharmacokinetics and antitumor efficacy of the photodynamic sensitizer 2-[1-hexyloxyethl]-2-devinyl pyropheophorbide-a, *J. Photochem. Photobiol. B: Biol.* 20: 55-61 (1993).
Birchler et al., "Selective Targeting and Photocoagulation of Ocular Angiogenesis Mediated by a Phage-Derived Human Antibody Fragment", *Nature Biotechnol.*, 17:984-988 (1999).
Blaauwgeers et al., "Polarized Vascular Endothelial Growth Factor Secretion by Human Retinal Pigment Epithelium and Localization of Vascular Endothelial Growth Factor Receptors on the Inner Choriocapillaris", *American Journal of Pathology*, 155(2): 421-428 (1999).
Boulton et al., "VEGF localization in diabetic retinopathy", *Br J Ophthalmol*, 82:561-568 (1998).
Brower, V., "Tumor Angiogenesis—New Drugs on the Block", *Nature Biotechnol.* 17:963-968 (1999).
Casalini et al., "Tumor Pretargeting: Role Of Avidin/Streptavidin On Monoclonal Antibody Internalization", *J.Nuclear Med.*, 38(9):1378-1381 (1997).
Cattel et al., "The Role of Conjugation Processes and Linking Agents in the Preparation of Molecular/Particulate Conjugates—a Review", *S.T.P Pharma. Sci.*, 9(4):307-319 (1999).
Certified English Translation of Japanese Kokai [Unexamined Patent] No. 53-84998, "Carcinostatic Method."
Certified English Translation of Japanese Kokai [Unexamined Patent] No. 57-185220, "Anti-Cancer Drug Having Chlorophyll Derivative Effective Component."
Certified English Translation of: Fischer, H. et al., "[On the Bromination of the Esters of Mesoisochlorin e4 and Mesochlorin e6]," *Berischte der Deutschen Chemischen* 75:1778-1795 (1942).
Chen et al., "New Technology for Deep Light distribution in Tissue for Phototherapy", *The Cancer J.*, 8(2):154-163 (2002).
Chen et al., "New directions in photodynamic therapy," *ICCP-2. 2nd International Conference on Porphyrins and Phthalocyanines*, Jun. 30, 2002-Jul. 5; Kyoto, Japan: 78 [abstract S-26].
Chen, J., "Next Generation Light Delivery System for Multi-Treatment Extended Duration Photodynamic Therapy (MED-PDT)", *SPIE-Proceedings Series*, 2972:161-167 (1997).
Ciulla et al., "Changing therapeutic paradigms for exudative age-relted macular degeneration: antiangiogenic agents and photodynamic therapy", *Exp. Opin. Invest. Drugs*, 8(12):2173-2182 (1999).
Dartsch et al., "Photodynamic therapy of vascular stenoses? Response of cultured human smooth muscle cells from non-atherosclerotic arteries and atheromatous plaques following treatment with photosensitizing porphyrins", *Proc. SPIE-INT. Soc. Opt. Eng.*, 1462:77-80 (1990).

Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3):230-234 (1995).

De Jode, et al., "A comparison of Novel Light Sources for Photodynamic Therapy", *Lasers Med Sci*, 12:260-268 (1997).

Derwent English Abstract, Accession No. 1996-475153, citing Russian Patent RU 2054944 C, published Feb. 27, 1996, "Production of purpurin-18 for treatment of tumours—comprises extracting vegetable waste with ethanol, oxidative splitting, degreasing and purifying".

Devoisselle, et al., "Effect of indocyanin green formulation on blood clearance and in vivo fluorescence kinetic profile of skin," *Proc. SPIE* 2627:100-108 (1995).

Dillon et al., "*In Vitro* and *In Vivo* Protection Against Phototoxic Side Effects of Photodynamic Therapy by Radioprotective Agents WR-2721 and WR-77913", *Photochem. Photobiol.*, 48(2):235-238 (1988).

Dimitroff et al., "Anti-angiogenic activity of selected receptor tyrosine kinase inhibitors, PD166285 and PD173074: Implications for combination treatment with photodynamic therapy", *Investigational New Drugs*, 17:121-135 (1999).

Dougherty et al., Review "Photodynamic Therapy", *J. Natl. Cancer Inst.*, 90(12):889-905 (1998).

Dougherty et al., Yearly Review "Photodynamic Therapy", *Photochem. Photobiol.*, 58(6):895-900 (1993).

Dougherty, T.J., "A Brief History of Clinical Photodynamic Therapy Development at Roswell Park Cancer Institute", *J. Clin. Laser Med. & Surg.*, 14(5):219-221 (1996).

Dougherty, T.J., Photosensitization of malignant tumors, *Seminars in Surgical Oncology* 2:24-37 (1986).

Fact Sheet: Laser Medical Pac, pp. 1-2 (1998).

Ferrario et al., "Antiangiogenic Treatment Enhances Photodynamic Therapy Responsiveness in a Mouse Mammary Carcinoma", *Cancer Research*, 60:4066-4069 (2000).

Fischer, H. et al., "[On the Bromination of the Esters of Mesoisochlorin $e_4$ and Mesochlorin $e_6$]," *Berischte der Deutschen Chemischen* 75:1778-1795 (1942).

Fisher, W.G. et al. "Simultaneous Two-Photon Activation of Type-1 Photodynamic Therapy Agents," *Photochem. Photobiol.*, 66(2):141-155 (1997).

Freiherr, G., "Advances in Photodynamic Therapy Lure Device Innovators", *Medical Device & Diagnostic Industry*, http://feedback@devicelink.com, 4 pages.

Gagel, M. P., Photodynamic therapy with porphyrins (1997), available at http://www.dermatology.org/laser.pdt.html.

Gilson et al., "Therapeutic ratio of photodynamic therapy in the treatment of superficial tumours of skin and subcutaneous tissues in man", *J. Cancer*, 58:665-667 (1988).

Granville et al., "Photodynamic Treatment with Benzoporphyrin Derivative Monoacid Ring A Produces Protein Tyrosine Phosphorylation Events and DNA Fragmentation in Murine P815 Cells", *Photochem. Photobiol.*, 67(3):358-362 (1998).

Haas et al., "Phototherapy of Bladder Cancer: Dose/Effect Relationships", Journal of Urology, 136:525-258 (1986).

Haslam et al., "Recent Developments in Methods for the Esterification and Protection of the Carboxyl Group," *Tetrahedron* 36: 2409-2433 (1980).

Henderson et al., An *in vivo* quantitative structure-activity relationship for a congeneric series of pyropheophorbide derivatives as photosensitizers for photodynamic therapy, *Cancer Research* 57: 4000-4007 (1997).

Jacka et al., "A Lamp for Cancer Phototherapy", *Aust. J. Phys.*, 36:221-226 (1983).

Jiang et al., "Enhanced photodynamic killing of target cells by either monoclonal antibody or low density lipoprotein mediated delivery systems", *J. Controlled Release*, 19:41-58 (1992).

Jiang et al., "Selective Depletion of a Thymocyte Subset *in Vitro* with an Immunomodulatory Photosensitizer", *Clin. Immunol.*, 91(2):178-87 (1999).

Jones et al. "Photodynamic therapy for patients with advanced non-small-cell carcinoma of the lung," *Clin Lung Cancer.* 3(1):37-41 (2001).

Kashtan et al., "Photodynamic Therapy of Colorectal Cancer Using a New Light Source from In Vitro Studies to a Patient Treatment", *Dis. Colon. Rectum.*, 39(4):379-383 (1996).

Kessel et al., Photosensitization with bacteriochlorins, *Photochem. Photobiol.* 58(2): 200-203 (1993).

Kozyrev et al., Effect of substituents in $OsO_4$ reactions of metallochlorins regioselective synthesis of isobacteriochlorins and bacteriochlorins, *Tetrahedron Letters* 37(22): 3781-3784 (1996).

Kreimer-Birnbaum, M., "Modified Porphyrins, Chlorins, Phthalocyanines, and Purpurins: Second-Generation Photosensitizers for Photodynamic Therapy", *Seminars in Hematology* 26(2):157-173 (1989).

Li et al., "Application of Ruppert's reagent in preparing novel perfluorinated porphyrins, chlorins and bacteriochlorins", *J. Chem. Soc. Perkin Trans* 1, 1785-1787 (1999).

Lin et al., "Skin Necrosis due to Photodynamic Action of Benzoporphyrin Depends on Circulating Rather than Tissue Drug Levels: Implications for Control of Photodynamic Therapy", *Photochem. Photobiol.*, 68(4):575-583 (1998).

Lourwood, D.L., "The pharmacology and therapeutic utility of bisphosphonates," *Pharmacotherapy* 18(4):779-789.

Mackie, et al., "In vivo canine coronary artery laser irradiation: photodynamic therapy using dihematoporphyrin ether and 632 nm laser. A safety and dose-response relationship study" *Lasers Surg Med.* 11:535-544 (1991).

Marcus, S.L., "Photodynamic Therapy of Human Cancer", *Proceedings of the IEEE*, 80(6):869-899 (1992).

Margaron et al., "Photodynamic therapy inhibits cell adhesion without altering integrin expression", *Biochimica et Biophysica Acta*, 1359:200-210 (1997).

McMillan et al., "Tumor growth inhition and regression induced by photothermal vascular targeting and angiogenesis inhibitor retinoic acid", *Cancer Lett.*, 137:35-44 (1999).

Meerovich et al., "Photosensitizer for PDT based on phosphonate phthalocyanine derivative", *Proc. SPIE-INT. Scc. Opt. Eng.*, 2924:86-90 (1996).

Mew et al., "Ability of Specific Monoclonal Antibodies and Conventional Antisera Conjugated to Hematoporphyrin to Label and Kill Selected Cell Lines Subsequent to Light Activation", *Cancer Res.*, 45:4380-4386 (1985).

Mew et al., "Photoimmunotherapy: Treatment of animal Tumors with Tumor-Specific Monoclonal Antibody-Hematoporphyrin Conjugates", *J. Immunol.*, 130(3):1473-1477 (1983).

Millson et al., "Ex-Vivo Treatment of Gastric Helicobacter Infection by Photodynamic Therapy ", *J. of Photochemistry and Photobiology B: Biology*, 32:59-65 (1996).

Mizeret, et al., "Cylindrical Fiberoptic Light Diffuser for Medical Application ", *Lasers Surg. Med.*, 19:159-167 (1996).

Nakatani et al., "Chemistry and biochemistry of Chinese drugs. VII. Cytostatic pheophytins from silkworm excreta, and derived photocytoxic pheophorbides", *Chem. Pharm. Bull.*, 29(8):2261-2269 (1981).

Nemoto, R. et al., "Inhibition by a new bisphosphate (YM175) of bone resorption induced by the MBT-2 tumour of mice," *British Journal of Cancer* 67(5):893-897 (1993).

North et al., "Viral Inactivation in Blood and Red Cell Concentrates with Benzoporphyrin Derivative", *Blood Cells* 18:129-140 (1992).

Pandey et al., "Shedding some light on tumours", *Chem. Indust.*, 1998:739-743 (1998).

Pandey et al., Comparative in vivo sensitizing efficacy of porphyrin and chlorin dimers joined with ester, ether, carbon-carbon or amide bonds, *J. Molecular Recognition* 9: 118-122 (1996).

Papapoulos, S.E., "Bisphosphonates: structure-activity relations from a clinical perspective," *Medicina* 57(Suppl. 1):61-64 (1997).

Parrish, J.A., "Photobiologic Consideration in Photoradiation Therapy" *Porphyrin Photosensitization*, Kessel, D. and T.M. Dougherty (Eds.) New York: Plenum Press, 1983 pp. 91-108.

Patent Abstract of Japan citing Japanese Patent Application JP 09124652, published May 13, 1997, "Porphyrin Derivative and Use Thereof".

Pittau et al., "An Inexpensive Light Source for Oncologic Photodynamic Therapy", *IEEE Eng. Med. Biol.*, pp. 105-106 (1998).

Prewett et al., "Antivascular Endothelial Growth Factor Receptor (Fetal Liver Kinase 1) Monoclonal Antibody Inhibits Tumor Angiogenesis and Growth of Several Mouse and Human Tumors", *Cancer Research*, 59:5209-5218 (1999).

Renno et al., "Photodynamic Therapy Using Lu-Tex Induces Apoptosis In Vitro, and Its Effect is Potentiated by Angiostatin in Retinal Capillary Endothelial Cells", *Investigative Opthalmol. & Visual Sci.*, 41(12):3963-3971 (2000).

Rimington et al., Preparation and photosensitizing properties of hematoporphyrin ethers, *Free Rad. Res. Comms.* 7(3-6): 139-142 (1989).

Ruebner, A. et al. "Carrier Systems in PDT II: Accumulation Strategies of Biotin-Avidin Coupled Photosensitizers Developed On Cultured Tumor Cells," *SPIE*, 2625:328-32 (1996).

Rungta et al., Purpurinimides as photosensitizers: effect of the presence and position of the substituents in the *in vivo* photodynamic efficacy, *Bioorg. Medicinal Chem. Letters* 10: 1463-1466 (2000).

Savellano et al., "Pegylated BPD Verteporfin C225 Anti-EGF Receptor Direct Covalent Linkage Photosensitizer Immunoconjugates", *Photochem. Photobiol.*, 69:38S (1999).

Savitsky, A.P. et al. "Avidin-Biotin System for Targeting Delivery of Photosensitizers and Other Cytotoxic Agents Into Malignant Tissues," *SPIE*, 3191: 343-53 (1997).

Schmidt-Erfurth et al., "In Vivo Uptake of Liposomal Benzoporphyrin Derivative and Photothrombosis in Experimental Corneal Neovascularization", *Lasers in Surgery and Medicine*, 17:178-188 (1995).

Schmidt-Erfurth et al., "Photodynamic Therapy of Experimental Choroidal Melanoma Using Lipoprotein-delivered Benzoporphyrin", *Opthalmol.*, 101:89-99 (1994).

Schmidt-Erfurth et al., "Photodynamic therapy of subfoveal choroidal neovascularization: clinical and angiographic examples", *Graefe's Arch. Clin. Exp. Opthamol.*, 236:365-74 (1998).

Schmidt-Erfurth et al., "Vascular targeting in photodynamic occlusion of subretinal vessels", *Opthalmol.*, 101(12):1953-1961 (1994).

Sharman et al., "Novel water-soluble phthalocyanines substituted with phosphonate moieties on the benzo rings", *Tetrahedron Lett.*, 37(33):5831-5834 (1996).

Sharman, W.M. et al., "Novel water-soluble phthalocyanines substituted with phosphonate moieties in the benzo rings," Tetrahedron Letters 37(33):5831-5834 (1996).

Sigsestad, C.P. et al. "Chemical Modification of Normal Tissue Damage Induced by Photodynamic Therapy," *Brit. J. Cancer* 74(Suppl. 37):S89-92 (1996).

Smith et al, "Meso substitution of chlorophyll derivatives: direct route for transformation of bacteriopheophorbides *d* into bacteriopheophorbides *c*," *J Am Chem Soc* 107:4946-54 (1985).

Smith et al., "Bacteriochlorophylls c from *Chloropseudomonas ethylicum*. Composition and NMR Studies of the Pheophorbides and Derivatives", Am. Chem. Soc., 102(7):2437-2448 (1980).

Spikes, J.D., Porphyrins and related compounds as photodynamic sensitizers, *Annals of the New York Academy of Sciences* 244: 496-508 (1975).

Sternberg et al. "Porphyrin-based Photosensitizers for Use in Photodynamic Therapy", *Tetrahedron*, 54:4151-4202 (1998).

Su, F., Photodynamic Therapy: A Maturing Medical Technology, OE-Reports, SPIE, Feb. 2000, available at http://www.spie.org/web/oer/february/feb00/phototherapy.html.

Szeimies et al., "A New Light Source for PDT of Skin Lesions", http://www.lumacare.com/paper3.htm, 2 pages (after 1993).

Szeimies et al., "A Possible New Incoherent Lamp for Photodynamic Treatment of Superficial Skin Lesions", *Acta Derm Venereal*, 74:117-119 (1994).

Tomio et al., "Effect of Hematoporphyrin and Red Light on AH-130 Solid Tumors in Rats", *ACTA Radiologica Oncol.*, 22:49-53 (1983).

Umemura et al., "Recent Advances in Sonodynamic Approach to Cancer Therapy," *Ulrasonics Sonochemistry*, 3:S187-S191 (1996).

Warwick, R.I., "Infinite Machines' Subsidiary Receives Positive Results in Photodynamic Therapy Tests", *BW HealthWire*, http://biz.yahoo.com/bw/97/06/18/imci_y000_1.html, 2 pages (1997).

Whitehurst et al., "Development of an Alternative Light Source to Lasers for Photodynamic Therapy: 1. Comparative In Vitro dose Response Characteristics", *Lasers in Med. Sci.*, 8:259-267 (1993).

Wieman et al., "(418) Photodynamic Therapy (PDT) of Locally Recurrent Breast Cancer (LRBC) with Lutetium Texaphyrin (Lutrin)", *American Society of Clinical Oncology*, 18:111A (1999).

Wilder-Smith et al., "(G1546) Photoeradication of *Helicobacter pylori* in Humans: Phase 1 Study", *AGA Abstracts Gastroenterology*, 116(4):A354 (1999).

Woodburn et al., Evaluation of porphyrin characteristics required for photodynamic therapy, *Photochem. Photobiol.* 55(5): 697-704 (1992).

Yamamoto et al., "Photodynamic effects on the nucleic acids of cancer cells sensitized by sodium phytoclorin", *Medicine and Biology*, 90(6):397-400, English translation and certificate of translation included, 4 pages (Jun. 10, 1975).

Yamamoto et al., "Photoradiation therapy, phytochlorin and visible light", *Prevention and Detection of Cancer, Part 1, Prevention. Volume 2, Etiology-Prevention Methods*, Proceedings of the Third International Symposium on Detection and Prevention of Cancer held Apr. 26, 1976 in New York, N.Y., 1(2):1789-1802 (1978).

Yamamoto, T., "Effect of phytochlorin on transplantable cancer cells", *Medicine and Biology*, 89(6):433-438, English translation and certificate of translation included, 7 pages (Dec. 10, 1974).

Yamamoto, T., "Suppression of tumors by the photodynamic action of phytochlorin sodium", *Medicine and Biology*, 90(4):161-164, English translation and certificate of translation included, 4 pages (Apr. 10, 1975).

Yumita et al., "Sonodynamically Induced Antitumor Effect of Gallium-Porphyrin Complex by focused Ultrasound on Experimental Kidney Tumor", *Cancer Letters*, 112:79-86 (1997).

Yumita et al., "The Combination Treatment of Ultrasound and Antitumor Drugs on Yoshida Sarcoma", *Japan J. Hyperthermic Oncol.*, 3(2):175-182 (1987).

Zheng et al., "Photosensitizers Related to Purpurin-18-N-alkylimides: A Comparitive in vivo Tumoricidal Ability of Ester versus Amide Functionalities", *Biorganic & Med. Chem. Letts.*, 10:123-127 (2000).

Zheng et al., "Chlorin-based symmetrical and unsymmetrical dimers with amide linkages: effect of the substituents on photodynamic and photophysical properties," *J. Chem. Soc. Perkins 1*, pp. 3113-3121 (2000).

* cited by examiner

NONINVASIVE VASCULAR THERAPY

RELATED APPLICATIONS

This application is a divisional of and claims priority to U.S. application Ser. No. 09/905,777, filed Jul. 13, 2001, to James Chen, and entitled "NONINVASIVE VASCULAR THERAPY", which claims benefit of priority under 35 U.S.C. §119(e) to U.S. Provisional Application Ser. No. 60/116,235, entitled "NONINVASIVE VASCULAR THERAPY" to James Chen, filed Jan. 15, 1999. The subject matter of each of U.S. Provisional Application Ser. No. 60/116,235 and U.S. application Ser. No. 09/905,777 is incorporated in its entirety by reference.

TECHNICAL FIELD OF THE INVENTION

This invention relates generally to the field of medicine and pharmacotherapeutics with photosensitizing agents or other energy activated agents. Specifically, this invention relates to methods, compounds, compositions and kits useful for site specific delivery to a lesion target site of a therapeutically effective amount of a photosensitizing agent that is activated by a relatively low fluence rate of light over a prolonged period of time. This invention further relates to the use of either an external or internal light source effective in providing transcutaneous photodynamic therapy as a treatment modality for atherosclerotic lesions and restenotic lesions in vivo.

BACKGROUND OF THE INVENTION

One form of energy activated therapy is photodynamic therapy (PDT). PDT has been applied to the vascular system to treat atherosclerotic lesions and restenotic lesions in vivo.

PDT is performed by first administering a photosensitive compound systemically or topically, followed by illumination of the treatment site at a wavelength or waveband which closely matches the absorption spectra of the photosensitizer. In doing so, singlet oxygen and other reactive species are generated leading to a number of biological effects resulting in cytotoxicity. The depth and volume of the cytotoxic effect in tissue depends on the complex interactions of light penetration in tissue, the photosensitizer concentration and cellular location, and availability of molecular oxygen.

Vascular lesions are typically treated by light delivered from within the vessel by a fiber optic probe as described by Mackie et al. (Lasers in Surgery and Medicine 11:535-544 (Wiley-Liss, Inc. 1991). Since light is delivered from within the lumen of the vessel, the vessel by necessity must be punctured in order to introduce the optical fiber. Puncture of an arterial vessel is associated with various medical risks including, downstream embolization from intravascular dislodgement of plaque or other debris; bleeding of the puncture site at the skin or vessel; heparinization may cause bleeding or other side effects; intimal flap from passage of the optical fiber causing downstream infarction; repeat procedures pose increased total risk; infection from the optical fiber; thrombosis of the treated vessel; aneurysm formation; and perforation of the vessel wall. Furthermore, invasive PDT has other disadvantages such as inability to treat small vessel disease where the vessel(s) cannot be treated because the vessel diameter is too small and where it is unsafe to subject the patient to an invasive procedure which may increase risk of complications especially where infection and bleeding disorders pre-exist.

A large number of PDT light sources and methods of use have been described. However, reports describing the sources and effects of transcutaneous light delivery for PDT purposes are more limited. It has generally been accepted that the ability of a light source external to the body to cause clinically useful cytotoxicity is limited in depth to a range of 1-2 cm or less depending on the photosensitizer. Treatment of superficial tumors in this manner may be associated with inadvertent skin damage due to accumulation of the photosensitizer in the skin which is a property of all systemically administered sensitizers in clinical use. For example, clinically useful porphyrins such as Photophrin® (QLT, Ltd. brand of sodium porfimer) are associated with photosensitivity lasting up to 6 weeks. Purlytin®, which is purpurin and Foscan® which is a chlorin sensitize the skin for several weeks. Indeed, efforts have been made to develop photoprotectants to reduce skin photosensitivity (see: Dillon et al., Photochemistry and Photobiology, 48(2): 235-238, 1988; and Sigdestad et al., British J. of Cancer, 74:S89-S92, 1996). In fact, PDT protocols involving systemic administration of photosensitizer require that the patient avoid sunlight and bright indoor light to reduce the chance of skin phototoxic reactions.

Recently, it has been claimed that with a sufficiently intense laser external light source causing two-photon absorption by a photosensitizer, it is theoretically possible to cause a very limited volume of cytotoxicity transcutaneously at greater depths. However, no clinical studies exist to support this contention. One would expect that the passage of an intense beam of light through the skin would lead to the same risk of injury to non-target tissues, such as skin and subcutaneous tissue, if used in conjunction with a systemically administered photosensitizer.

For example, one PDT modality discloses the use of an intense laser source to activate drug within a precisely defined boundary (see: Fisher et al., "Method for improved selectivity in photo-activation of molecular agents," U.S. Pat. No. 5,829, 448). The two-photon methodology requires a high power laser for drug activation with a highly collimated beam that requires a high degree of spatial control. For a large tumor this treatment is not practical since the beam would have to be swept across the skin surface in some sort of set, repeatable pattern over time. Patient or organ movement would be a problem, because the beam could become misaligned. Non-target tissue or skin and subcutaneous tissue photosensitivity is not addressed in the literature available. Any sensitizer in the path of the beam would be activated and cause unwanted collateral tissue damage. The present disclosure is a one-photon method and therefore teaches away from the two-photon method. Further, the present invention teaches and enables the prolonged exposure at a lower fluence rate, which promotes the protection of non-target tissue or skin and subcutaneous normal tissue and reduces collateral tissue damage.

Other modalities have employed the use of low total fluence of PDT delivered over a short time period to avoid skin photoactivation and the use of drug administration timing methods to enable destruction of small tumors in animals (see: U.S. Pat. No. 5,705,518 (Richter et al.). However, the present disclosure teaches away from this method in order to enable large total fluence PDT, but at a lower fluence rate, which enables the treatment of larger tumor volumes. Richter et al. further fails to teach or disclose the suggestion of a targeting scheme as presently disclosed.

In the event that the target lesion lies below an intact cutaneous layer, the main drawbacks of all transcutaneous illumination methods, whether they be external laser or external nonlaser light sources, are: 1) the risk of damage to non-target tissues, such as the more superficial cutaneous and subcutaneous tissues overlying the target lesion, 2) limitation of treatment volume, and 3) limitation of treatment depth. Damage to normal tissue between the light source and the target occurs due to the uptake of photosensitizer by the skin and other tissues overlying the lesion with resultant unwanted photoactivation in these tissues. The consequences of inadvertent skin damage caused by transcutaneous light delivery to a subcutaneous lesion may include severe pain, serious infection, and fistula formation. The limited volume of a target lesion that can be clinically treated and the limitations of the light penetration below the skin surface in turn have limited clinical transcutaneous PDT to superficial, thin lesions.

Clearly, there would be significant advantage to a completely noninvasive form of PDT directed to subcutaneous vascular lesions which avoids the inadvertent activation of photosensitizer in skin and intervening tissues and also avoids damaging the vessel walls. To date, this feasibility has not been clinically demonstrated nor realized. Only in animal studies utilizing mice or other rodents with very thin cutaneous tissue layers, have very small superficial subcutaneous malignant tumors been treated. These in vivo studies do not enable or teach the safe application of transcutaneous light sources to treat atherosclerotic lesions and restenotic lesions in humans, however.

This invention further discloses the selective binding of the photosensitizing agent to specific target tissue antigens, such as those found on the surface of or within vascular lesions. This targeting scheme decreases the amount of sensitizing drug required for effective therapy, which in turn reduces the total fluence, and the fluence rate needed for effective photoactivation. For example, the highly specific uptake of photosensitizer in atherosclerotic vessels using the avidin-biotin system would result in reduced or no skin uptake enabling safe transcutaneous photoactivation. While there are several reports in the scientific literature of utilizing the specificity of the bind between biotin and streptavidin to target tumor cells, there are no reports utilizing this ligand-receptor binding pair aimed at vascular lesions nor in conjunction with prolonged PDT light exposure (see, for example: Savitsky et al., SPIE, 3191: 343-353, 1997; and Ruebner et al., SPIE, 2625: 328-332, 1996). In a non-PDT modality, the biotin-streptavidin-receptor binding pair has also been reported as tumor targeting conjugates with radionuclides (see: U.S. Pat. No. 5,630, 996 (Reno et al.) and with monoclonal antibodies (see: Casalini et al; J. Nuclear Med., 38(9): 1378-1381, 1997) and U.S. Pat. No. 5,482,698 (Griffiths)).

Other ligand-receptor binding pairs have been used in PDT for targeting tumor antigens, but also fail to teach their use in conjunction with blood vessel targeting or treatment of atherosclerotic and restenotic lesions (see: for example Mew et al., J. of Immunol., 130(3): 1473-1477, 1983).

A light source far less intense than a high powered laser is used (see: W. G. Fisher, et al., Photochemistry and Photobiology, 66(2): 141-155, 1997). The present disclosure teaches the unexpected use of a low power non-coherent light source utilized for longer than about 2 hours to increase photoactivation depth. This teaches away from the use of a high powered, brief exposure using collimated light as disclosed in W. G. Fisher et al., Photochemistry and Photobiology, 66(2): 141-155, 1997.

Clearly, there is a need to improve the method of transcutaneous PDT to enable the safe and practical application of transcutaneous light to vascular lesions in large and small blood vessels without risking damage to non-target tissues, such as skin and normal subcutaneous tissue. The present disclosure teaches a method of photoactivation and photosensitizer construct which improves on the prior art by enabling PDT induced cytotoxicity on both macro- and microscopic scales without risk to the cutaneous layer. Also, the therapeutic index is enhanced due to a specific targeting scheme.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

SUMMARY OF THE INVENTION

The present invention is based on the precise targeting of photosensitive agents or other energy activated agents, drugs and compounds to specific target cells or compositions of a subject or patient and to the method of activation of these targeted photosensitizer agents or other energy activated agents by subsequently administering to the subject light or ultrasonic energy at a relatively low intensity rate and over a prolonged period of time, utilizing a light or ultrasonic energy source that is either external or internal to the target tissues in order to achieve maximal cytotoxicity with minimal side effects.

One embodiment of the present invention is drawn to a method for transcutaneous photodynamic therapy ("PDT") of a vascular lesion in a mammalian subject comprising: administering to the subject a therapeutically effective amount of a photo-sensitizing agent or a photosensitizing agent delivery system or a prodrug, where the photosensitizing agent or photosensitizing agent delivery system or prodrug selectively binds to the target issue which is an atherosclerotic plaque. This step is followed by irradiating at least a portion of the subject with light at a wavelength or waveband absorbed by the photosensitizing agent or if a prodrug, by a prodrug product thereof, where the light is provided by a light source, and where the irradiation is at a relatively low fluence rate results in the activation of the photosensitizing agent or prodrug product. In this embodiment of the present invention, the photosensitizing agent or photosensitizing agent delivery system or prodrug is cleared from non-target tissues of the subject prior to irradiation.

One other embodiment of the present invention is drawn to a method for transcutaneous PDT of a target composition in a mammalian subject comprising: administering to the subject a therapeutically effective amount of a photosensitizing agent or a photosensitizing agent delivery system or a prodrug, where the photosensitizing agent or photosensitizing agent delivery system or prodrug selectively binds to the target composition. This step is followed by irradiating at least a portion of the subject with light at a wavelength or waveband absorbed by the photosensitizing agent or if a prodrug, by a prodrug product thereof, where said light is provided by a light source, and where the irradiation is at a relatively low fluence rate that results in the activation of the photosensitizing agent or said prodrug product. This embodiment contemplates that the photosensitizing agent or the photosensitizing agent delivery system or prodrug is cleared from non-target tissues of the subject prior to said irradiation. This embodiment also contemplates that light is delivered from a relatively low power noncoherent or coherent light source that is positioned in proximity to the diseased vessel, beneath the skin surface and external to the diseased blood vessel. Another preferred embodiment of the present invention is drawn to a method of transcutaneous PDT of a target tissue in a mammalian subject as described above, where the light source is entirely external to the patient's intact skin layer.

Another embodiment of this invention is drawn to a method of transcutaneous PDT, where the photosensitizing agent is conjugated to a ligand. One preferred embodiment of this invention contemplates a method of transcutaneous PDT, where the ligand is an antibody specific to thick or thin neointimas, arterial plaques, vascular smooth muscle cells and/or the abnormal extracellular matrix of the site to be treated. Other preferred embodiments include methods of transcutaneous PDT, where the ligand is a peptide or polymer specific to thick or thin neointimas, arterial plaques, vascular smooth muscle cells and/or the abnormal extracellular matrix of the site to be treated.

A still further embodiment of the present invention is drawn to a method of transcutaneous PDT, where the photosensitizing agent is selected from the group consisting of: indocyanine green (ICG); methylene blue; toluidine blue; aminolevulinic acid (ALA); chlorin compounds; phthalocyanines; porphyrins; purpurins; texaphyrins; and any other agent that absorbs light in a range of 500 nm-1100 nm. A preferred embodiment of this invention contemplates that the photosensitizing agent is indocyanine green (ICG).

One other embodiment of the present invention is drawn to a method of transcutaneous PDT, where the activation of the photosensitizing agent will likely occur within 30 minutes to 72 hours of irradiation, more preferably within 60 minutes to 48 hours of irradiation and most preferably within 3 hours to 24 hours of irradiation. Of course, clinical testing will be required to determine the optimal illumination time. In addition, it is contemplated that the total fluence delivered will preferably be between 30 Joules to 25,000 Joules, more preferably be between 100 Joules and 20,000 Joules, and most preferably be between 50 Joules to 10,000 Joules. Clinical testing will determine the optimal total fluence required to reduce the atheroma and undesirable tissue causing restenotic lesions.

A still further embodiment of this invention is drawn to a method for transcutaneous photodynamic therapy of target lesion in a mammalian subject comprising: administering to the subject a therapeutically effective amount of a first conjugate comprising a first member of a ligand-receptor binding pair conjugated to an antibody or antibody fragment, where the antibody or antibody fragment selectively binds to a target antigen found on thick of thin neointimas, arterial plaques, vascular smooth muscle cells and/or the abnormal extracellular matrix of the site to be treated. This step is followed by administering to the subject a therapeutically effective amount of a second conjugate comprising a second member of the ligand-receptor binding pair conjugated to a photosensitizing agent or photosensitizing agent delivery system or prodrug, where the first member binds to the second member of the ligand-receptor binding pair. A subsequent step includes irradiating at least a portion of the subject with light at a wavelength or waveband absorbed by the photosensitizing agent or if prodrug, by the product thereof. This embodiment further includes that the light is provided by a light source and that the irradiation is at a relatively low fluence rate that results in the activation of the photosensitizing agent or prodrug product.

Still further preferred embodiments of this invention are drawn to methods of transcutaneous PDT where the ligand-receptor binding pair is selected from the group consisting of: biotin-streptavidin; and antigen-antibody. A further preferred embodiment of the present invention is drawn to the presently disclosed methods where the antigens are vasculature antigens of the vascular lesion and the preferable ligand-receptor binding pair includes biotin-streptavidin. In this preferred embodiment, the activation of photosensitizer agents by a relatively low fluence rate light source over a prolonged period of time results in the destruction or reduction of the vascular lesion.

Another preferred embodiment contemplates a transcutaneous PDT method where the photosensitizing agent delivery system comprises a liposome delivery system consisting essentially of the photosensitizing agent.

Yet another embodiment of the present invention is drawn to a method for transcutaneous ultrasonic therapy of a target lesion in a mammalian subject comprising administering to the subject a therapeutically effective amount of an ultrasonic sensitizing agent or a ultrasonic sensitizing agent delivery system or a prodrug, where the ultrasonic sensitizing agent or ultrasonic sensitizing agent delivery system or prodrug selectively binds to the thick or thin neointimas, arterial plaques, vascular smooth muscle cells and/or the abnormal extracellular matrix of the site to be treated. This step is followed by irradiating at least a portion of the subject with ultrasonic energy at a frequency that activates the ultrasonic sensitizing agent or if a prodrug, by a prodrug product thereof, where the ultrasonic energy is provided by an ultrasonic energy emitting source. This embodiment further provides that the ultrasonic therapy drug is cleared from non-target tissues of the subject prior to irradiation.

A preferred embodiment of this invention contemplates a method for transcutaneous ultrasonic therapy of a target tissue, where the target tissue is a lesion in the vascular system.

Other preferred embodiments of this invention contemplate that the ultrasonic energy emitting source is external to the patient's intact skin layer or is inserted underneath the patient's intact skin layer, but is external to the blood vessel to be treated. An additional preferred embodiment of this invention provides that the ultrasonic sensitizing agent is conjugated to a ligand and more preferably, where the ligand is selected from the group consisting of: a target lesion specific antibody; a target lesion specific peptide and a target lesion specific polymer. Other preferred embodiments of the present invention contemplate that the ultrasonic sensitizing agent is selected from the group consisting of indocyanine green (ICG); methylene blue; toluidine blue; aminolevulinic acid (ALA); chlorin compounds; phthalocyanines; porphyrins; purpurins; texaphyrins; and any other agent that absorbs light in a range of 500 nm-1100 nm. A preferred embodiment of this invention contemplates that the photosensitizing agent is indocyanine green (ICG).

Other embodiments of the present invention are drawn to the presently disclosed methods of transcutaneous PDT, where the light source is positioned in proximity to the target tissue of the subject and is selected from the group consisting of: an LED light source; an electroluminescent light source; an incandescent light source; a cold cathode fluorescent light source; organic polymer light source; and inorganic light source. A preferred embodiment includes the use of an LED light source.

Yet other embodiments of the presently disclosed methods are drawn to use of light of a wavelength that is from about 500 nm to about 1100 nm, preferably greater than about 650 nm and more preferably greater than about 700 nm. A preferable embodiment of the present method is drawn to the use of light that results in a single photon absorption mode by the photosensitizing agent.

Additional embodiments of the present invention include compositions of photosensitizer targeted delivery system comprising: a photosensitizing agent and a ligand that binds a receptor on the target tissue with specificity. Preferably, the photosensitizing agent of the targeted delivery system is conjugated to the ligand that binds a receptor on the target lesion with specificity. More preferably, the ligand comprises an antibody that binds to a receptor. Most preferably, the receptor is an antigen on thick or thin neointimas, arterial plaques, vascular smooth muscle cells and/or the abnormal extracellular matrix of the site to be treated.

A further preferred embodiment of this invention contemplates that the photosensitizing agent is selected from the group consisting of indocyanine green (ICG); methylene blue; toluidine blue; aminolevulinic acid (ALA); chlorin compounds; phthalocyanines; porphyrins; purpurins; texaphyrins; and any other agent that absorbs light in a range of 500 nm-1100 nm.

Still another preferred embodiment of this invention contemplates that the ligand-receptor binding pair is selected from the group consisting of: biotin-streptavidin; and antigen-antibody.

Yet another preferred embodiment contemplates that the photosensitizing agent comprises a prodrug. Other embodiments of the presently disclosed invention contemplate methods for transcutaneous PDT to destroy a target cell in a mammalian subject comprising: administering to the subject a therapeutically effective amount of a photosensitizing agent or a photosensitizing agent delivery system or a prodrug, where the photosensitizing agent or photosensitizing agent delivery system or prodrug selectively binds to the target cell. This step is followed by irradiating at least a portion of the subject with light at a wavelength or waveband absorbed by the photosensitizing agent or if prodrug, by a prodrug product thereof, where the light is provided by a light source, and where the irradiation is at a relatively low fluence rate that results in the activation of the photosensitizing agent or prodrug product and the destruction of the target cell. This embodiment contemplates that the photosensitizing agent is cleared from non-target tissues of the subject prior to said irradiation.

DETAILED DESCRIPTION OF THE INVENTION

This invention provides methods and compositions for treating a target tissue or destroying or impairing a target cell or composition in a mammalian subject by the specific and selective binding to the target tissue, cell or composition of a photosensitizer agent. This method comprises irradiating at least a portion of the subject with light at a wavelength absorbed by said photosensitizing agent that under conditions of activation during photodynamic therapy using a relatively low fluence rate, but an overall high total fluence dose results in minimal collateral tissue damage.

Terms as used herein are based upon their art recognized meaning and from the present disclosure should be clearly understood by the ordinary skilled artisan. For sake of clarity, terms may also have particular meaning as would be clear from their use in context. For example, transcutaneous more specifically herein refers to the passage of light through unbroken tissue. Where the tissue layer is skin or dermis, transcutaneous includes transdermal and the light source is external to the outer skin layer. However, where transillumination refers herein to the passage of light through a tissue layer, such as the outer layer of a blood vessel, the light source is external to the blood vessel, but internal or implanted into the subject or patient.

Specifically, the present invention is based on the precise targeting of photosensitive agents or drugs and compounds to specific target antigens of a subject or patient and to the method of activation of targeted photosensitizer agents by subsequently administering to the subject light of a relatively low fluence rate over a prolonged period of time from a light source that is external to the target tissue in order to achieve maximal cytotoxicity or reduction of plaque or abnormal intima with minimal side effects or collateral tissue damage.

Further, as used herein "target cells" or "target tissues" are those cells or tissues, respectively that are intended to be impaired or destroyed by this treatment method. Target cells or target tissues take up the photosensitizing agent; then when sufficient radiation is applied, these cells or tissues are impaired or destroyed. Target cells are those cells in target tissues, which include, but are not limited to vascular lesions, thick or thin neointimas, arterial plaques, neoplasms, vascular smooth muscle cells and the abnormal extracellular matrix of the site to be treated. "Non-target cells" are all the cells of an intact animal which are not intended to be impaired or destroyed by the treatment method. These non-target cells include but are not limited to healthy blood cells, and other normal tissue, not otherwise identified to be targeted.

"Destroy" is used to mean kill the desired target cell. "Impair" means to change the target cell in such a way as to interfere with its function. For example, North et al. observed that after exposure to light of benzoporphyrin derivatives ("BPD")-treated, virus-infected T cells, holes developed in the T cell membrane, which increased in size until the membrane completely decomposed (Blood Cells 18:129-40, 1992). Target cells are understood to be impaired or destroyed even if the target cells are ultimately disposed of by macrophages.

"Photosensitizing agent" is a chemical compound which homes to one or more types of selected target cells and, when contacted by radiation, absorbs the light, which results in impairment or destruction of the target cells. Virtually any chemical compound that homes to a selected target and absorbs light may be used in this invention. Preferably, the chemical compound is nontoxic to the animal to which it is administered or capable of being formulated in a nontoxic composition. Preferably, the chemical compound in its photodegraded form is also nontoxic. A comprehensive listing of photosensitive chemicals may be found in Kreimer-Birnbaum, Sem. Hematol. 26:157-73, 1989. Photosensitive compounds include, but are not limited to, chlorins, bacteriochlorins, phthalocynanines, porphyrins, purpurins, merocyanines, psoralens, benzoporphyrin derivatives (BPD) and porfimer sodium and pro-drugs such as δ-aminolevulinic acid, which can produce drugs such as protoporphyrin. Other compounds include indocyanine green (ICG); methylene blue; toluidine blue; texaphyrins; and any other agent that absorbs light in a range of 500 nm-1100 nm.

"Radiation" as used herein includes all wavelengths. Preferably, the radiation wavelength is selected to match the wavelength(s) which excites the photosensitive compound.

Even more preferably, the radiation wavelength matches the excitation wavelength of the photosensitive compound and has low absorption by the non-target cells and the rest of the intact animal, including blood proteins. For example, the preferred wavelength for ICG is the range of 750-850 nm.

The radiation is further defined in this invention by its intensity, duration, and timing with respect to dosing with the photosensitive agent. The intensity or fluence rate must be sufficient for the radiation to penetrate skin and reach the target cells, target tissues or target compositions. The duration or total fluence dose must be sufficient to photoactivate enough photosensitive agent to act on the target cells. Both intensity and duration must be limited to avoid overtreating the animal. Timing with respect to dosing with the photosensitive agent is important, because 1) the administered photosensitive agent requires some time to home in on target cells and 2) the blood level of many photosensitive agents decreases rapidly with time.

This invention provides a method of treating an animal, which includes, but is not limited to, humans and other mammals. The term "mammals" or a "mammalian subject" also includes farm animals, such as cows, hogs and sheep, as well as pet or sport animals such as horses, dogs and cats.

By "intact animal" is meant that the whole, undivided animal is available to be exposed to radiation. No part of the animal is removed for separate radiation, in contrast with photophoresis, in which the animal's blood is circulated outside its body for exposure to radiation. The entire animal need not be exposed to radiation. Only a portion of the intact animal subject may or need be exposed to radiation.

"Transcutaneously" is used herein as meaning through the skin of an animal subject.

Briefly, the photosensitizing agent is generally administered to the animal before the animal is subjected to radiation.

Preferred photosensitizing agents include, but are not limited to, chlorins, bacteriochlorins, phthalocyanines, porphyrins, purpurins, merocyanines, psoralens and pro-drugs such as δ-aminolevulinic acid, which can produce drugs such as protoporphyrin. More preferred are methylene blue, toluidine blue, texaphyrins and any other agent that absorbs light in a range of 500 nm-1100 nm. Most preferred is indocyanine green (ICG) (for example, see: WO 92/00106 (Raven et al.); WO97/31582 (Abels et al.) and Devoisselle et al., SPIE 2627: 100-108, 1995).

The photosensitizing agent is administered locally or systemically. The photosensitizing agent is administered orally or by injection which may be intravenous, subcutaneous, intramuscular or intraperitoneal. The photosensitizing agent also can be administered externally or topically via patches or implants.

The photosensitizing agent also can be conjugated to specific ligands reactive with a target, such as receptor-specific ligands or immunoglobulins or immunospecific portions of immunoglobulins, permitting them to be more concentrated in a desired target cell or microorganism. The photosensitizing agent may be further conjugated to a ligand-receptor binding pair, which includes, but is not limited to: biotin-streptavidin; and antigen-antibody. This conjugation may permit lowering of the required dose level since the material is more selectively targeted and less is wasted in distribution into other tissues whose destruction must be avoided.

The photosensitizing agent can be administered in a dry formulation, such as pills, capsules, suppositories or patches. The photosensitizing agent also may be administered in a liquid formulation, either alone with water, or with pharmaceutically acceptable excipients, such as are disclosed in Remington's Pharmaceutical Sciences. The liquid formulation also can be a suspension or an emulsion. In particular, liposomal or lipophilic formulations are most desirable. If suspensions or emulsions are utilized, suitable excipients include water, saline, dextrose, glycerol, and the like. The compositions may contain minor amounts of nontoxic auxiliary substances such as wetting or emulsifying agents, antioxidants, pH buffering agents, and the like.

The dose of photosensitizing agent will vary with the target cell(s) sought, the optimal blood level (see Example 1), the animal's weight and the timing of the radiation. Depending on the photosensitizing agent used, an equivalent optimal therapeutic level will have to be established. Preferably, the dose is calculated to obtain a blood level between about 0.001 and 100 μg/ml. Preferably, the dose will obtain a blood level between about 0.01 and 10 μg/ml.

This method comprises irradiating at least a portion of the subject with light at wavelength or waveband absorbed by said photosensitizing agent that under conditions of activation during photodynamic therapy using a relatively low fluence rate, but also at an overall high total fluence dose resulting in minimal collateral tissue damage. It is contemplated that the optimal total fluence will be determined clinically using a light dose escalation trial. It is further contemplated that the total fluence will preferably be in the range of 30 Joules to 25,000 Joules, and more preferably be in the range from 100 Joules to 20,000 Joules, and most preferably be in the range from 500 Joules to 10,000 Joules. The methods comprise irradiating at least a portion of the subject with light at a wavelength or waveband absorbed by said photosensitizing agent that under conditions of activation during photodynamic therapy using a relatively low fluence rate, but an overall high total fluence dose resulting in minimal collateral normal tissue damage. What is meant by "relatively low fluence rate" is a fluence rate that is lower than that typically used and one that generally does not result in significant damage to collateral or non-target tissues. Specifically, the intensity of radiation used to treat the target cell or target tissue is preferably between about 50 and 100 mW/cm$^2$. Most preferably, the intensity of radiation is between about 15 and 50 mW/cm$^2$.

The duration of radiation exposure is preferably between about 30 minutes and 72 hours. More preferably, the duration of radiation exposure is between about 60 minutes and 48 hours. Most preferably, the duration of radiation exposure is between about 2 hours and 24 hours.

The total number of Joules delivered to the treatment site is contemplated to lie between 30 J-25,000 J, more preferably between 100 J-20,000 J, and most preferably between 500 J-10,000 J.

Of course, clinical testing will be required to determine the optimal fluence rate and total fluence delivered to the treatment site.

While not wishing to be limited by a theory, the inventor proposes that a photosensitizer agent can be substantially and selectively photoactivated in the target cells and target tissues within a therapeutically reasonable period of time and without excess toxicity or collateral damage to non-target tissues. Thus, there appears to be a therapeutic window bounded by the photosensitizer agent dosage and radiation dosage. The formation of photodegradation products of a photosensitizer agent was used as an indicator of photoactivation. Photoactivation of a photosensitizer agent has been postulated to cause the formation of singlet oxygen, which has a cytotoxic effect.

Additionally, the present invention is drawn to a method for transcutaneous ultrasonic therapy of tumors in a mammalian subject or patient by first administering to the subject a therapeutically effective amount of a first conjugate comprising a first member of a ligand-receptor binding pair conjugated to an antibody or antibody fragment, wherein said antibody or antibody fragment selectively binds to a target antigen of thick or thin neointimas, arterial plaques, vascular smooth muscle cells and/or the abnormal extra-cellular matrix of the site to be treated; and simultaneously or subsequently administering to the subject a therapeutically effective amount of a second conjugate comprising a second member of the ligand-receptor binding pair conjugated to an ultrasonic sensitizing agent or ultrasonic sensitizing agent delivery system or prodrug, wherein the first member binds to the second member of the ligand-receptor binding pair. These steps are followed by irradiating at least a portion of the subject with energy at a wavelength absorbed by said ultrasonic sensitizing agent or if ultrasonic sensitizing agent delivery system, by the product thereof, wherein said energy is provided by an energy source that is external to the subject; and wherein said ultrasound is at a relatively low intensity rate that results in the activation of said ultrasonic sensitizing agent or prodrug product.

While a preferred embodiment of the present invention is drawn to the use of light energy in a light or photodynamic therapy of tumors using light or photosensitizer agents, other forms of energy are within the scope of this invention and understandable by one of ordinary skill in the art. Such forms of energy include, but are not limited to: thermal; sonic; ultrasonic; chemical; photo or light; microwave; ionizing, such as: x-ray, and gamma ray; and electrical. For example, sonodynamically induced or activated agents include, but are not limited to: gallium-porphyrin complex (see Yumita et al., Cancer Letters, 112: 79-86, 1997); other porphyrin complexes, such as protoporphyrin and hematoporphyrin (see Umemura et al., Ultrasonics Sonochemistry 3:S187-S191, 1996); other cancer drugs, such as daunorubicin and adriamycin, used in the presence of ultrasound therapy (see Yumita et al., Japan J. Hyperthermic Oncology, 3(2): 175-182, 1987).

This invention further contemplates the use of an energy source, preferably a light source, that is external to the target tissue. The target tissues may include and may relate to the atherosclerotic lesions, restenotic lesions and the lesion antigens, per se. These target lesion antigens would be readily understood by one of ordinary skill in the art therefore to include but to not be limited to: tumor surface antigen; tumor endothelial antigen; non-tumor endothelial antigen; tumor vessel wall antigen; neointimal antigens; arterial plaque antigens; and vascular smooth muscle cell antigens.

The ordinary skilled artisan would be familiar with various ligand-receptor binding pairs, including those known and those currently yet to be discovered. Those known, include, but are not limited to the group consisting of biotin-streptavidin; and antigen-antibody. This invention contemplates a preferred embodiment that includes the use of biotin-streptavidin as the ligand-receptor binding pair. However, the ordinary skilled artisan would readily understand from the present disclosure that any ligand-receptor binding pair may be useful provided the ligand-receptor binding pair demonstrate a specificity for the binding by the ligand to the receptor and further provided that the ligand-receptor binding pair permit the creation of a first conjugate comprising a first member of the ligand-receptor binding pair conjugated to an antibody or antibody fragment, wherein said antibody or antibody fragment selectively binds to a target antigen of thick or thin neointimas, arterial plaques, vascular smooth muscle cells and/or the abnormal extracellular matrix of the site to be treated; and further permit the creation of a second conjugate comprising a second member of the ligand-receptor binding pair conjugated to an energy sensitizing or photosensitizing agent or energy sensitizing or photosensitizing agent delivery system or prodrug, and further wherein the first member binds to the second member of the ligand-receptor binding pair.

A preferred embodiment of the present invention is drawn to a method where the photosensitizing agent delivery system includes a liposome delivery system consisting essentially of the photosensitizing agent, however the ordinary skilled artisan would readily understand from the present disclosure that other delivery systems may be used. A still further and preferred embodiment of the present invention contemplates the disclosed method where the photosensitizing agent delivery system utilizes both a liposome delivery system and a photosensitizing agent, where each is separately conjugated to a second member of the ligand-receptor binding pair, and where the first member binds to the second member of the ligand-receptor binding pair, and more preferably where the ligand-receptor binding pair is biotin-streptavidin. This embodiment further contemplates that the photosensitizing agent as well as the photosensitizing agent delivery system may both be specifically targeted through the selective binding to a target tissue antigen by the antibody or antibody fragment of the first member binding pair. Such dual targeting is envisioned to enhance the specificity of uptake and to increase the quantity of uptake.

Having now generally described the invention the same will be more readily understood through reference to the following examples which are provided by way of illustration, and are not intended to be limiting of the present invention, unless specified.

EXAMPLE 1

Transcutaneous Photodynamic Therapy of Vascular Lesions

Occlusive peripheral vascular disease, restenosis and other vascular lesions may be effectively treated by transcutaneous photodynamic therapy. Restenosis, the formation of a thick neointima due to the accumulation of proliferative smooth muscle cells and extracellular matrix at an injured site, is a frequent complication of surgical and percutaneous interventions for occlusive peripheral vascular disease. Restenosis occurs as a result of the natural reparative process and is proportional to the degree of injury inflicted upon the arterial wall. The current therapies include surgery, administration of anticoagulants such as Heparin®, vasoconstrictors such as Angiotensin II®, antiproliferative agents such as Angiopeptin®, Maphthopyran and Mycophenolate mofetil.

Since Heparin® has a high-binding capacity to basic fibroblast growth factor and is also a potent antiproliferative agent and Angiotensin II® is a polypeptide that induces vasoconstriction by binding to receptors on vascular smooth muscle cells, Heparin® or Angiotensin II® may be used to localize a photosensitizer agent to the vascular region in a mammalian subject to be treated. Alternatively, the photosensitizer may be conjugated to LDL, VLDL, or a similar agent that specifically binds to arterial plaques and/or vascular lesions.

Therefore, a photosensitizer agent is conjugated to a Heparin®, Angiotensin II®, LDL, VLDL, or a similar agent which binds selectively to the thick neointimas, arterial plaques, neoplasms, vascular smooth muscle cells and/or the extracellular matrix of the site to be treated. Excess photosensitizer conjugates are eliminated from the body. One or more light sources are strategically placed or implanted near the tissue to be treated. Following a sufficient amount of time to permit clearing of the conjugates from the non-target tissues, the light sources are activated, irradiating the target tissue with a relatively low fluence rate, but high total fluence dose of light in the wavelength from about 750 nm to about 850 nm. The light may be applied internally or externally, with the external light source the preferred mode.

The specific dose of photosensitizer conjugate is that which results in a concentration of active ICG sufficient to obtain a blood level between about 0.001 and 100 µg/ml and more preferably, a dose of between about 0.01 and 10 µg/ml. However, it is well within the skill of the ordinary skilled artisan to determine the specific therapeutically effective dose using standard clinical practices and procedures.

Similarly, the specific fluence rate and total fluence dose may be routinely determined from the disclosure herein.

Additionally, the conjugate above could be further conjugated to an imaging agent such as technetium. Thus, the method could further comprise the steps of performing a nuclear medicine scan and imaging the vascular sites to be treated.

A targeted antibody-photosensitizer conjugate (APC) is constructed which binds selectively to antigens mainly present on neointimas, arterial plaques and/or vascular smooth muscle cells. This ligand-receptor binding pair or APC is infused intravenously and is taken up in the neointimas, arterial plaques, neoplasms, vascular smooth muscle cells and/or the extracellular matrix. When unbound, APC is eliminated from the body. Internal or external light sources may be used to activate the target drug.

Any number of antigens may be selected, provided that the antigen is specific for the neointimas, arterial plaques, neoplasms, vascular smooth muscle cells and/or the abnormal extracellular matrix. Such antigens would be known to those skilled in the art. The selection of a specific photosensitizer agent may be made, provided the photosensitizer agent is activated by a light wavelength of from 500 nm to 1100 nm, and more preferably a wavelength of 650 nm, and most preferably by a wavelength of 700 nm or greater. Such photosensitizer agents as provided in this disclosure are contemplated for use herein.

Figure 1A:
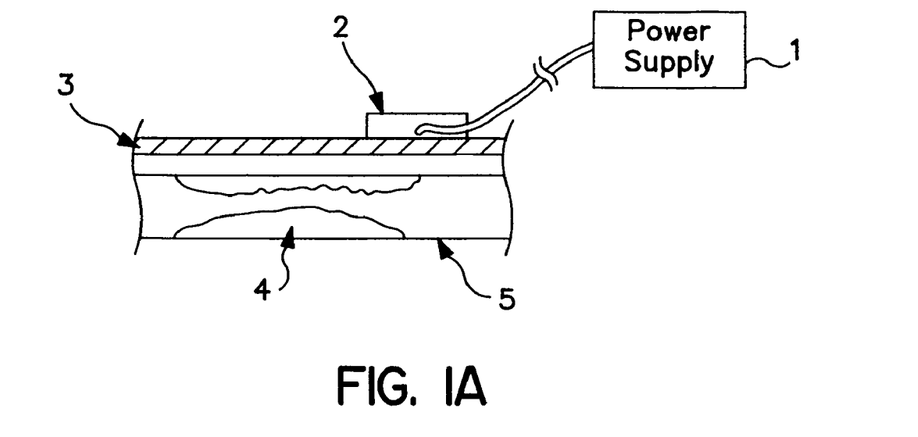
FIG. 1A shows a diagram that demonstrates transcutaneous PDT using a focused laser diode light source.
Figure 1B:
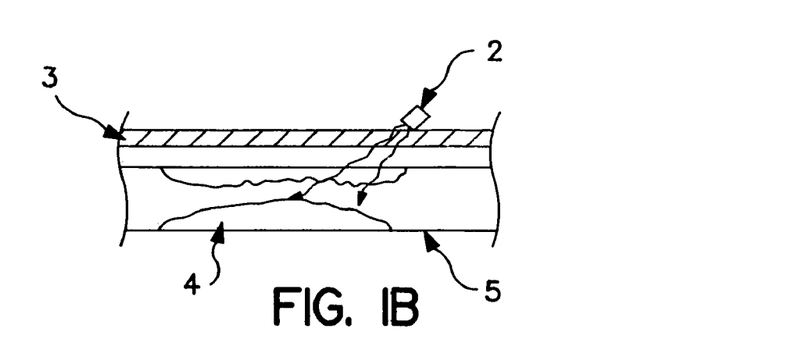
FIG. 1B shows PDT using a laser diode light source, where the light travels along the vessel wall to plaque with light scattering in plaque.

The PDT light source is an externally positioned light source directed at the site to be treated. The light source may be a laser diode (2), light emitting diode or other electroluminescent device. The light source is angled and the light beam is focused so as to direct the light through the skin (3) or membrane of the mammalian subject being treated in a direction lengthwise and parallel to the vessel wall (5) to plaque (4). See FIGS. 1A and 1B.

Figure 2:
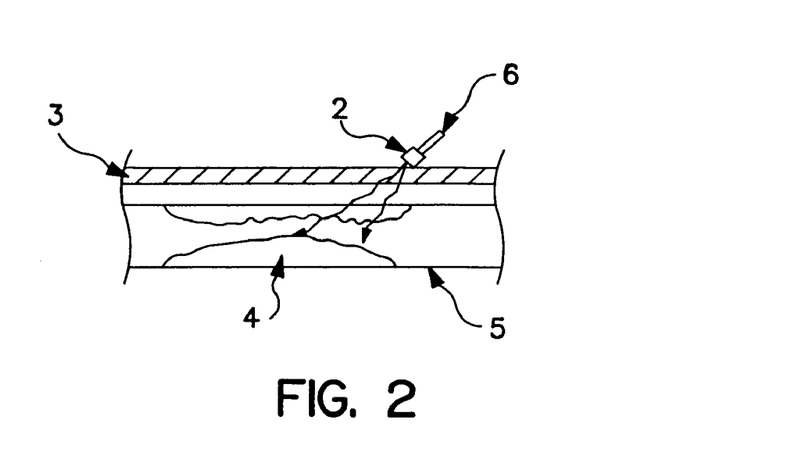
FIG. 2 shows PDT using an optical fiber delivery of light from a laser diode light source (not shown).
Figure 3:
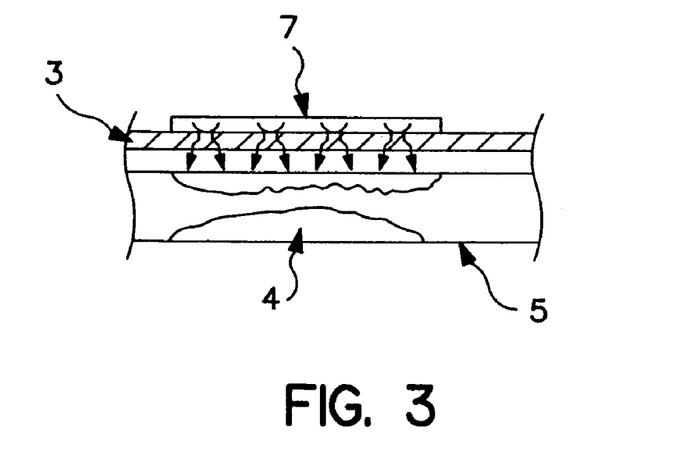
FIG. 3 shows PDT using an LED light source.
Figure 4:
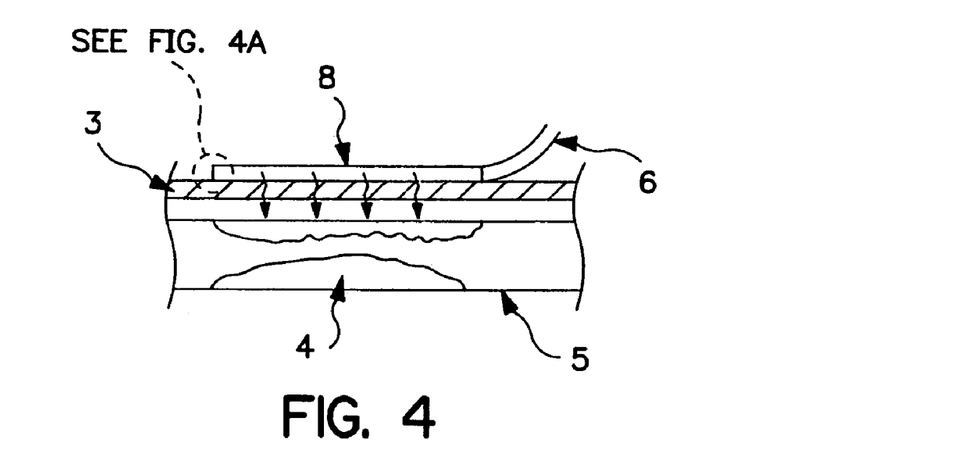
FIG. 4 shows PDT using an optical diffuser attached to an optical fiber with delivery of light from a laser diode light source (not shown).
Figure 4A:
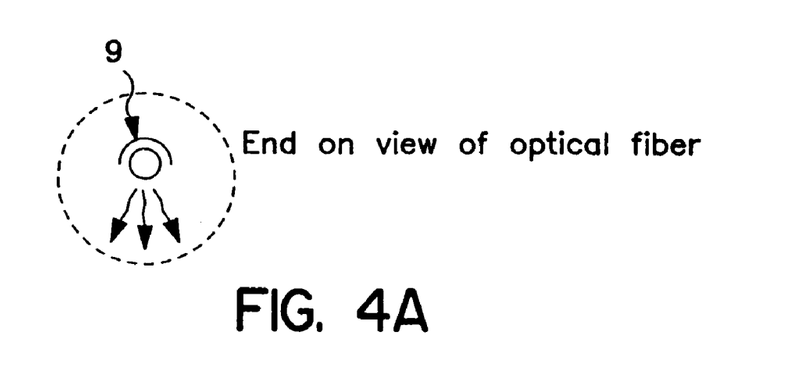

Alternatively, the light source could comprise a laser diode (2) coupled to an optical fiber (6) which is then aimed at the vessel so as to direct the light along the length of the vessel. See FIG. 2. The light source could also comprise a strip of light emitting diodes (LEDs) (7) which are then arrayed on the skin or the membrane overlying the site to be treated in the mammalian subject. See FIG. 3. The light source could also comprise an optical fiber diffuser (8) which is placed over the skin or the membrane overlying the site to be treated in the mammalian subject. See FIG. 4. A mirrored surface (9) may direct light downward.

As is apparent to one of ordinary skill in the art, the methods and compositions described above have various applications. For example, a group of small vessels in a mammalian subject may be treated by utilizing a patch composed of LEDs or a mat of woven optical fibers wherein the light source patch or mat is placed over the skin or the tissue overlying the site to be treated. Furthermore, the patch or mat could also contain pharmaceutical compositions or the photosensitizing agent which is then delivered by liposomal, transdermal or ionto- phoretic techniques. Additionally, vein grafts and artificial grafts could similarly be treated by the methods and compositions described above.

This invention has been described by a direct description and by examples. As noted above, the examples are meant to be only examples and not to limit the invention in any meaningful way. Additionally, one having ordinary skill in the art to which this invention pertains in reviewing the specification and claims which follow would appreciate that there are equivalents to those claimed aspects of the invention. The inventors intend to encompass those equivalents within the reasonable scope of the claimed invention.

What is claimed is:

1. An apparatus for light activated drug therapy of a target site of a subject, comprising:
   a patch adapted to be placed over the tissue at or overlying the target site to be treated, the patch comprising a photosensitizing agent; and
   a plurality of diodes physically coupled to and carried by the patch such that light outputted by the plurality of diodes is emitted from the patch towards the target site when at least one of the diodes is energized and the patch lies closely against the tissue at or overlying the target site so as to deliver at least a portion of the photosensitizing agent to the target site.

2. The apparatus of claim 1, wherein the plurality of diodes are a plurality of light emitting diodes.

3. The apparatus of claim 1, wherein the patch is configured to release a therapeutically effective amount of the photosensitizing agent.

4. The apparatus of claim 1, wherein the photosensitizing agent is formulated for delivery by a method selected from the group consisting of liposomal, transdermal and iontophoretic techniques.

5. The apparatus of claim 1, wherein the photosensitizing agent is selected from the group consisting of chlorins, bacteriochlorins, phthalocyanines, porphyrins, purpurins, merocyanines and psoralens.

6. The apparatus of claim 1, wherein the photosensitizing agent is selected from the group consisting of indocyanine green, methylene blue, lutetium texaphyrin, toludine blue and aminolevulinic acid.

7. The apparatus of claim 1, wherein the photosensitizing agent is indocyanine green.

8. The apparatus of claim 1, wherein at least one of the diodes is a laser diode.

9. The apparatus of claim 1, wherein the photosensitizing agent is selected from a group consisting of chlorins and chlorin compounds.

10. The apparatus of claim 1, wherein the photosensitizing agent is selected from a group consisting of toluidine blue and methylene blue.

11. An apparatus for light activated drug therapy of a target site of a subject, the apparatus comprising:
   an external patch adapted to be placed against the subject, the patch comprising a photosensitizing agent deliverable to the target site when the patch physically contacts the subject; and
   at least one light source carried by the patch, the at least one light source capable of receiving electrical energy and generating light using the electrical energy such that the light activates the photosensitizing agent at the target site.

12. The apparatus of claim 11, wherein the patch has a pair of opposing longitudinal sides and is adapted to output most of the light outputted by the at least one light source from one of the longitudinal sides placed against the subject.

13. The apparatus of claim 11, wherein the at least one light source includes a plurality of discrete light sources fixed to and aimed away from the patch.

14. The apparatus of claim 11, wherein the at least one light source is a plurality of light sources positioned between the target site and a portion of the patch when the patch physically contacts the subject.

15. The apparatus of claim 11, wherein the at least one light source comprises a strip of energizable light emitting devices.

16. The apparatus of claim 11, wherein the at least one light source comprises an electroluminescent light source.

17. The apparatus of claim 11, wherein the at least one light source comprises an organic polymer light source.

18. A patch for therapy of a target site of a subject, comprising:
 a photosensitizing agent deliverable from the patch to the target site when the patch contacts or overlays the target site of the subject; and
 an array of light sources capable of receiving electrical energy and generating light using the electrical energy, the array of light sources positioned with respect to the photosensitizing agent such that light generated by the array of light sources is delivered out of the patch so as to activate a portion of the photosensitizing agent that has been delivered to the target site.

19. The patch of claim 18, wherein the array of light sources is a strip of light emitting diodes that is directed at the target site when the patch contacts or overlays the target site of the subject.

20. The patch of claim 18, wherein the photosensitizing agent and the array of light sources are positioned such that a portion of the photosensitizing agent and light produced by the array of light sources are delivered from the patch to the target site of the subject while the patch contacts or overlays the target site of the subject.

21. The patch of claim 18, wherein the photosensitizing agent is adapted such that a therapeutically effective amount of the photosensitizing agent is delivered to the target site when the patch contacts or overlays the target site of the subject.

22. The patch of claim 18, wherein the photosensitizing agent is formulated for delivery by a method selected from a group consisting of liposomal techniques, transdermal techniques, and iontophoretic techniques.

23. The patch of claim 18, wherein at least one of the light sources is a diode.

24. The patch of claim 18, wherein at least one of the light sources is an electroluminescent light source.

25. The of claim 18, wherein at least one of the light sources is an organic polymer light source.

* * * * *

UNITED STATES PATENT AND TRADEMARK OFFICE
CERTIFICATE OF CORRECTION

PATENT NO. : 7,511,031 B2 Page 1 of 1
APPLICATION NO. : 10/899834
DATED : March 31, 2009
INVENTOR(S) : James Chen It is certified that error appears in the above-identified patent and that said Letters Patent is hereby corrected as shown below:

On the title page:
Item (62) & (60)
"(62) Division of application No. 09/905,777 filed on Jul. 13, 2001 (60) Provisional application No. 60/116,235, filed on Jan. 15, 1999" should read --(62) Division of application No. 09/905,777 filed on Jul. 13, 2001, which is a Continuation of PCT/US00/00852 filed on Jan. 14, 2000 (60) Provisional application No. 60/116,235, filed on Jan. 15, 1999--.

Item (56)
--WO 00/61584 10/2000-- should be added to face of patent.

Column 16
Line 24, "The of claim 18, wherein at least one of the light sources" should read --The patch of claim 18, wherein at least one of the light sources--.

Signed and Sealed this

Twenty-first Day of December, 2010

David J. Kappos
*Director of the United States Patent and Trademark Office*